US00PP18516P3

(12) United States Plant Patent

Yencho et al.

(10) Patent No.: US PP18,516 P3

(45) Date of Patent: Feb. 26, 2008

(54) SWEETPOTATO PLANT NAMED 'COVINGTON'

(50) Latin Name: *Ipomoea batatas*
Varietal Denomination: Covington

(75) Inventors: G. Craig Yencho, Raleigh, NC (US); Kenneth Pecota, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 238 days.

(21) Appl. No.: 11/225,431

(22) Filed: Sep. 13, 2005

(65) Prior Publication Data

US 2007/0061936 P1 Mar. 15, 2007

(51) Int. Cl.
*A01H 5/00* (2006.01)

(52) U.S. Cl. ..... Plt./258

(58) Field of Classification Search ..... Plt./258, Plt./395

See application file for complete search history.

(56) References Cited

PUBLICATIONS

Flier on 'NC98–08' from the North Carolina Sweetpotato Commission's Annual Meeting at the Wilson Cooperative Extension AgriCenter, Wilson NC, on Jan. 20, 2005.

*Primary Examiner*—Kent Bell

(74) *Attorney, Agent, or Firm*—Myers Bigel Sibley & Sajovec, P.A.

(57) ABSTRACT

*Ipomoea batatas* 'Covington' is an orange-fleshed, smooth-skinned, rose-colored, table stock sweetpotato. 'Covington' produces yields equal to 'Beauregard', the dominant sweetpotato variety produced in the United States, but it is 5-10 days later in maturity. The storage roots of 'Covington' are generally shorter and more uniformly shaped and fewer "jumbos" are produced as compared with 'Beauregard', resulting in higher "pack-out" by sweetpotato packers. The dry matter content of 'Covington' storage roots is slightly higher than that of 'Beauregard'. 'Covington' is also resistant to the russet crack strain of sweetpotato feathery mottle virus, moderately resistant to southern root knot nematode, and appears to be less sensitive genotype by environmental interactions (measured as an improved overall appearance score, and the percentage of culls and off-types present at harvest), all of which are considered to be major flaws in the variety 'Beauregard'. The flavor of the baked storage roots of 'Covington' has been judged to be excellent by standardized and informal taste panels. 'Covington' typically scores better in this regard when compared with 'Beauregard'.

7 Drawing Sheets

Latin name of the genus and species: The Latin name of the novel, plant variety disclosed herein is *Ipomoea batatas* (L.) Lam.

Variety denomination: The inventive cultivar of *Ipomoea batatas* disclosed herein has been given the varietal denomination 'Covington'.

BACKGROUND OF THE INVENTION

The sweetpotato (*Ipomoea batatas*) is a member of the morning glory family, *Convolvulaceae*. Sweetpotatoes produce an edible storage root that is developmentally and anatomically derived from root tissue. This contrasts with potatoes (*Solanum tuberosum*), which produce an edible tuber that is derived from an underground stolon and is similar in structure to an above-ground stem. New plantings of sweetpotato are commonly produced via two methods (1) vegetative stem cuttings taken from plants in the field or greenhouse, and (2) cuttings of sprouts (i.e. small plants) that arise from adventitious buds (i.e. buds that are not derived from meristematic tissue) produced from storage roots that have been planted in soil in three to five foot wide "plant beds" in the spring. These sprouts are cut and planted in the field using a mechanical transplanter. In contrast, potatoes are typically propagated from cut or whole tubers planted directly into the soil. New plants arising from the seed tubers are derived from the eye of the potato tuber, with each eye being equivalent to a stem node and consisting of a raised or depressed ridge or protuberance, bearing a scale-like leaf subtending a minute meristematic bud in its center and flanked by two leaf primordia.

The color of the flesh of the sweetpotato root varies with the cultivar and can range from white to orange to purple. Presently, the dominant sweetpotato variety produced in the United States is 'Beauregard' (unpatented). The present invention, a new and distinct sweetpotato variety named 'Covington', provides an improvement over 'Beauregard' in that it generally produces shorter and more uniformly shaped storage roots than 'Beauregard' and it appears to be less sensitive to genotype by environmental interactions, which is perceived to be a major flaw in 'Beauregard'. 'Covington' also typically scores as well as or better than 'Beauregard' in the flavor of its baked storage roots as measured by standardized and informal taste panels.

Lineage. 'Covington' originated from botanical seed harvested from the sweetpotato clone NC1528. NC1528 produces a vigorous vine similar to that of 'Covington'. A distinguishing feature of the vine of NC1528 is that it possesses leaf nodes that typically have purple pigmentation (187B); whereas, the internodes of 'Covington' do not. NC1528 also produces tan-orange to cream-orange colored storage roots (22C to 22D) with medium orange flesh (28B to 28C); whereas, the storage roots of 'Covington' are light to medium rose-colored (33D to 34D) that possess a similar flesh color (28B to 28C).

NC1528 was one of 26 genotypes present in the North Carolina State University (NCSU) Sweetpotato Breeding and Genetics Program's 1997 open-pollinated polycross *Streptomyces* soil rot (SSR) breeding nursery. The SSR breeding nursery was planted at the North Carolina Department of Agriculture and Consumer Service's (NCDA&CS) Central Crops Research Station in Clayton, Johnston County, North Carolina. The 26 genotypes present in the SSR breeding nursery were randomly mated; therefore, the male parent of 'Covington' is unknown. Seedlings from the SSR breeding nursery were planted in the NCSU Horticultural Sciences greenhouses in March of 1998. A single cutting was taken from each seedling and planted in the field in May of 1998 in an "on-farm" trial and selected as a "single-hill selection" on Sep. 9, 1998. A "single-hill selection" includes the storage roots derived from the single plant cutting, typically ranging from 2 to 15 storage roots with 2 to 10 storage roots from selected hills being saved for plant propagation the following year.

The "on-farm" trial was conducted in Green County near Kinston, N.C. 'Covington' was vegetatively increased, evaluated and advanced as the clone NC98-608; the "98" referring to the year in which 'Covington' was selected as a "single-hill" and the "608" indicating that the 'Covington' selection was the 608th "single-hill selection" made by the breeding program in 1998. Covington was first recognized as being potentially superior to 'Beauregard' after two further cycles of increase, and field and disease resistance evaluations at the NCDA&CS Horticultural Crops Research Station (HCRS), Clinton, N.C. and the NCSU Cunningham Research Station, Kinston, N.C. during 1999 and 2000.

Asexual Reproduction. 'Covington' has been asexually propagated via vegetative cuttings and/or storage root derived sprouts since its original selection in September 1998. Storage and plant bed propagation of the sweetpotatoes for sprout production was done at the NCDA&CS Horticultural Crops Research Station, Clinton, N.C. After two additional cycles of field selection as the clone NC98-608, 'Covington' was submitted to the NCSU Micropropagation Unit in order to eliminate viruses and pathogens via mericulture clean-up, and for subsequent tissue culture entry. The combination of characteristics disclosed herein for 'Covington' has remained stable, and the plant reproduces true-to-type through successive generations of asexual reproduction.

SUMMARY OF THE INVENTION

*Ipomoea batatas* 'Covington' is an orange-fleshed, smooth-skinned, rose-colored, table stock sweetpotato. 'Covington' produces yields equal to 'Beauregard', the dominant sweetpotato variety produced in the United States, but it is 5-10 days later in maturity. The storage roots of 'Covington' are generally shorter and more uniformly shaped and fewer "jumbos" are produced as compared with 'Beauregard', resulting in higher "pack-out" by sweetpotato packers. The dry matter content of 'Covington' storage roots is slightly higher than that of 'Beauregard'. 'Covington' is also resistant to the russet crack strain of sweetpotato feathery mottle virus and moderately resistant to southern root knot nematode, all of which are considered to be major flaws in the variety 'Beauregard'. The flavor of the baked storage roots of 'Covington' has been judged to be excellent by standardized and informal taste panels. 'Covington' typically scores as well as or better in this regard when compared with 'Beauregard'.

BRIEF DESCRIPTION OF THE DRAWINGS

The photographs in the drawings were made using conventional digital photographic techniques and show the colors as true as reasonably possible by conventional digital photography. Colors in the photographs may differ slightly from the color values cited in the detailed botanical description, which accurately describe the colors of the new *Ipomoea batatas*.

DETAILED BOTANICAL DESCRIPTION

The following is a detailed description of the botanical characteristics of a new and distinct cultivar of *Ipomoea batatas* plant known by the cultivar name *Ipomoea batatas* 'Covington'. In addition, a comparison of *Ipomoea batatas* 'Covington' with *Ipomoea batatas* 'Beauregard' is provided. For disease and pest resistance, the comparison also includes the *I. batatas* varieties 'Porto Rico' (unpatented) and 'Jewel' (unpatented).

Descriptors cited herein are based on standardized sweetpotato descriptors documented by the International Potato Center (CIP), Asian Vegetable Research & Development Center (AVRDC), and International Board for Plant Genetic Resources (IBPGR) in *Descriptors of Sweetpotato,* Huaman, Z. ed., IBPGR, Rome, Italy (1991). ISBN 92-9043-204-7. All colors cited herein refer to the color designations of the 2001 Edition of The Royal Horticultural Society Colour Chart, The Royal Horticulture Society, London, United Kingdom, except where general terms of ordinary dictionary significance are used. Where dimensions, sizes, colors and other characteristics are given, it is to be understood that such characteristics are approximations or averages set forth as accurately as practicable.

The descriptions and measurements reported herein are taken from field-grown plants 45 days after planting (DAP). The plants were grown at the NCDA&CS Horticultural Crops Research Station in Clinton, N.C. under commercial practice during June through October. 'Covington' has not been observed under all possible environmental conditions; therefore, the phenotype may differ somewhat with variations in the environment such as season, temperature, light intensity, day length, cultural conditions, and the like, without however any variance in the genotype.

The following discussion provides a description of the new cultivar of *Ipomoea batatas* 'Covington' as well as a comparison with other known varieties.

Plant Bed Production. Sprout production of 'Covington' on plant beds prior to cutting and transplanting in the field is as good as or slightly less than that of 'Beauregard', with transplant survival in the field generally being better than 'Beauregard'. Plants of 'Covington' derived from transplant beds are typically thicker with the average stem diameter for 'Covington' being 4.1 mm as compared with 'Beauregard', which is 3.5 mm in stem diameter (n=50). However, 'Covington' and 'Beauregard' produce similarly sized plants (20.1 mm and 20 mm in height, respectively; n=50) with the same number of nodes per cutting (both producing 8.9 nodes per cutting; n=50). During cool transplant production seasons 'Covington' produces shorter, stockier plants that are ready to cut roughly a week later as compared with 'Beauregard'. During hot transplant production seasons, these differences are not as evident.

Figure 1:
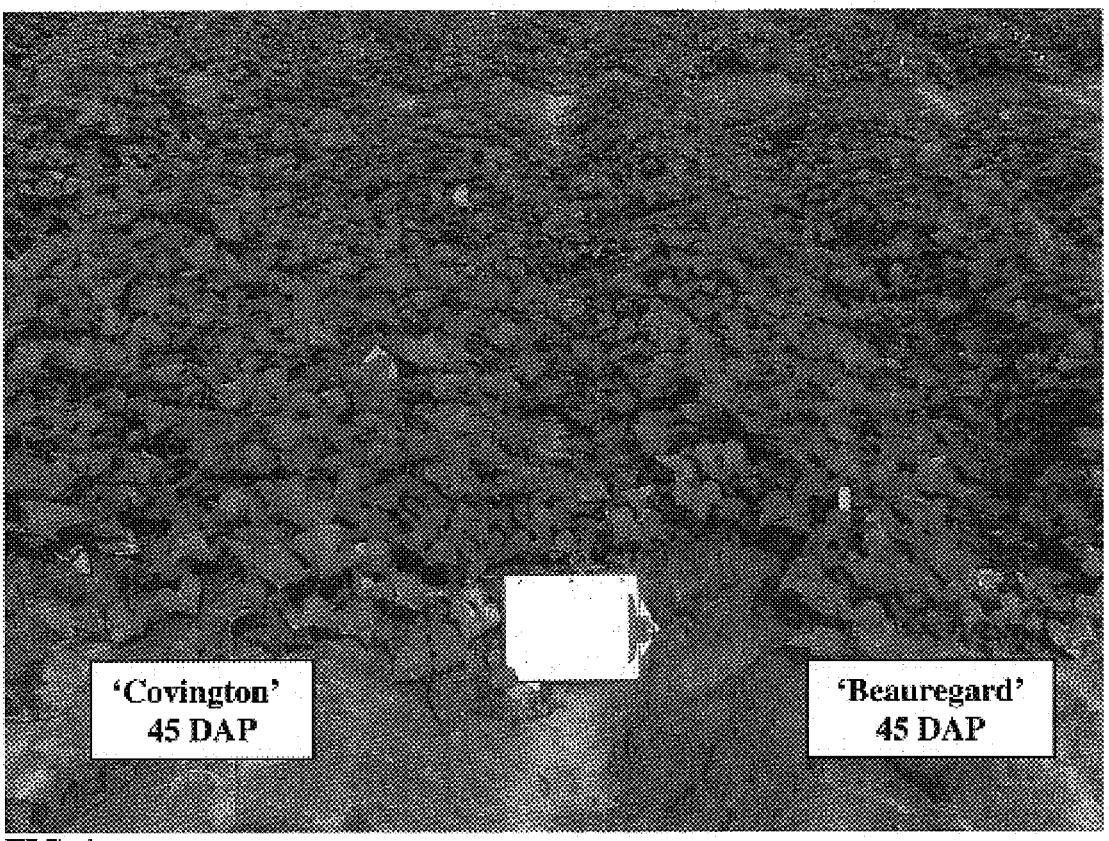
FIG. 1 is a color photograph of the canopy biomass produced by the new variety 'Covington' (2 rows on the left) and the variety 'Beauregard' (2 rows on the right) 45 days after planting at the HCRS, Clinton, N.C. in 2005.

Whole-plant Canopy Structure. FIG. 1 is a color photograph of the canopy biomass produced by the new variety 'Covington' and the variety 'Beauregard'. At 45 DAP both 'Covington' and 'Beauregard' typically have two main vines, with an average diameter at the base of 7.9 mm for 'Covington' and 7.1 mm for 'Beauregard'. At 50 cm from the base, the stem diameters are 6.1 mm and 5.2 mm, respectively. 'Covington' averaged 4.5 lateral branches per main vine as compared with 6.8 for 'Beauregard'. The stems of both 'Covington' and 'Beauregard' are green (144B). The length of the first internode beginning at the apex between the first and second fully developed leaves was similar, 47 mm for 'Covington' and 54 mm for 'Beauregard'. Covington produces a denser, more upright canopy that competes well against weeds in contrast to 'Beauregard', which produces a weaker spreading prostrate vine that does not compete as well against weeds. However, vine canopy in sweetpotatoes is greatly affected by soil fertility, and in highly fertile soils there may be no apparent difference in canopy cover.

Figure 2:
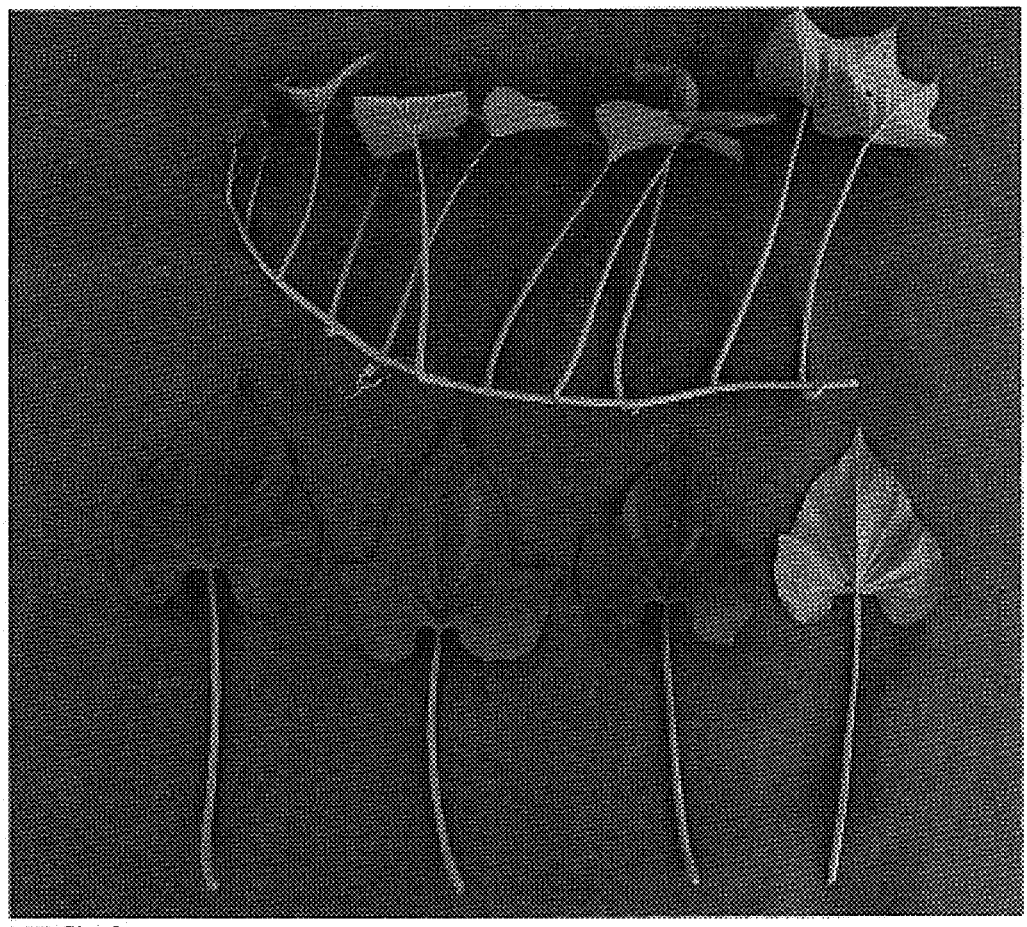
FIG. 2 is a color photograph showing typical leaves and a stem produced by 'Covington' 45 days after planting at the HCRS, Clinton, N.C. in 2005.
Figure 3:
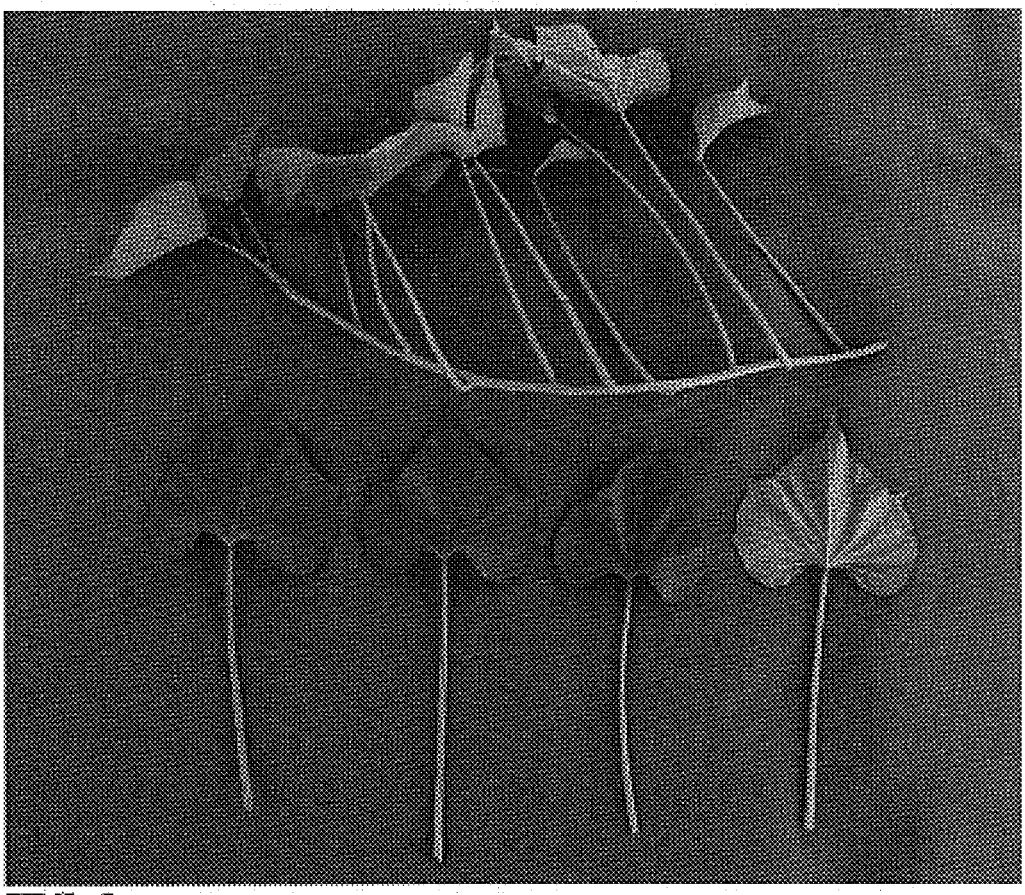
FIG. 3 is a color photograph showing typical leaves and a stem produced by 'Beauregard' 45 days after planting at the HCRS, Clinton, N.C. in 2005.

Foliage. The leaves of 'Covington' are alternate and simple in structure, and cordate to triangular in shape with no slight lobing (FIG. 2). The leaves have a smooth texture and matte finish. Mature leaf color for both 'Covington' and 'Beauregard' is green, between 147A and 147B on the upper surface and 147B on the lower surface. Young leaf color differs slightly in that 'Covington' has more purple pigmentation than 'Beauregard'. 'Covington' upper and lower leaf surfaces have a green base (147B) with secondary purple (N79A) while 'Beauregard' has a green base (147A) with secondary purple (N79B). 'Covington' leaves are both longer (135 mm versus 104 mm) and wider (140 mm versus 112 mm) on average than 'Beauregard'. On the lower leaf surface, 'Beauregard' has a purple (N79B) spot at the base of the main rib. Petioles are green (144B) with no secondary pigmentation in both 'Covington' and 'Beauregard'. Petiole length measured 231 mm for 'Covington' and 187 mm for 'Beauregard', and 'Covington' petioles were thicker at the base measuring 6.3 mm versus 5 mm for 'Beauregard'. Abaxial and adaxial veins are the same color as the leaf blade (147A to 147B) for both 'Covington' and 'Beauregard'.

TABLE 1

| Leaf | Upper Surface | | Lower Surface | |
|---|---|---|---|---|
| Structure | Covington | Beauregard | Covington | Beauregard |
| Young Leaf | Base 147B; Secondary N79A | Base 147A; Secondary N79B | Base 147B; Secondary N79A | Base 148A; Secondary N79B |
| Mature Leaf | Between 147A and 147B | Between 147A and 147B | 147B | 147B |

TABLE 1-continued

| Leaf | Upper Surface | | Lower Surface | |
|---|---|---|---|---|
| Structure | Covington | Beauregard | Covington | Beauregard |
| Petiole | 144B | 144B | N/A | N/A |
| Vine Color | 144B | 144B | N/A | N/A |

Figure 4:
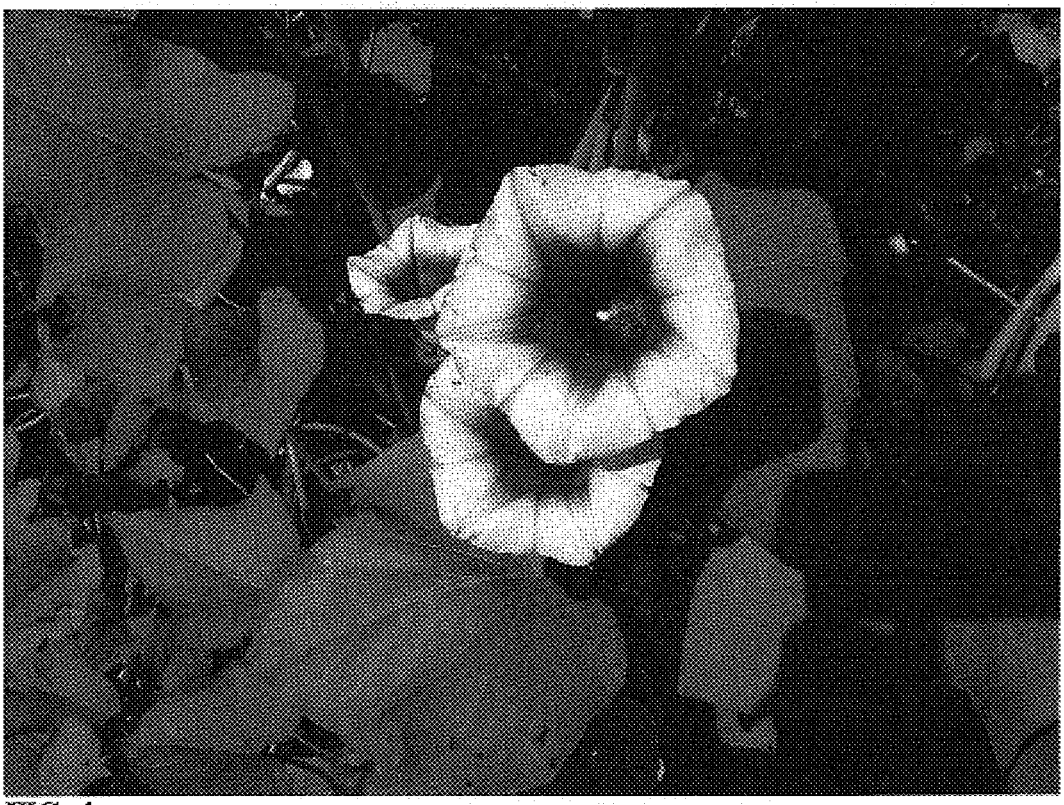
FIG. 4 is a color photograph showing a view of typical flowers of 'Covington'.
Figure 5:
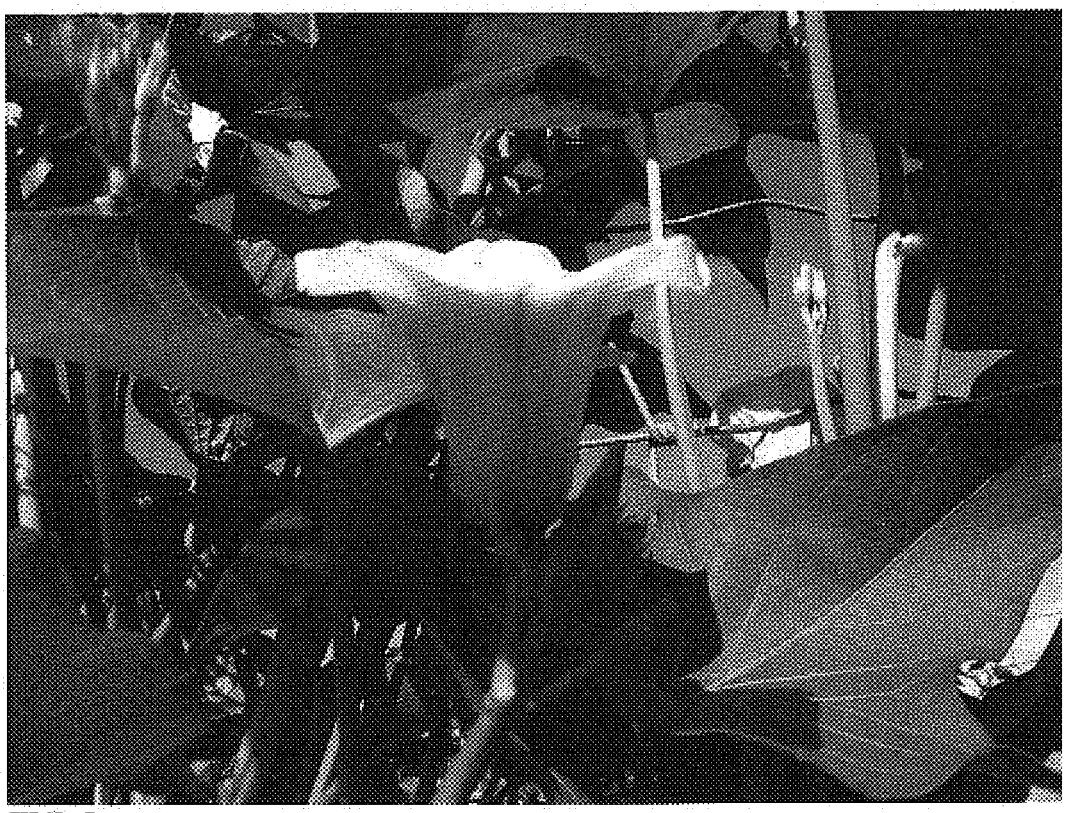
FIG. 5 is a color photograph showing a side view of a typical flower of 'Covington'.
Figure 6:
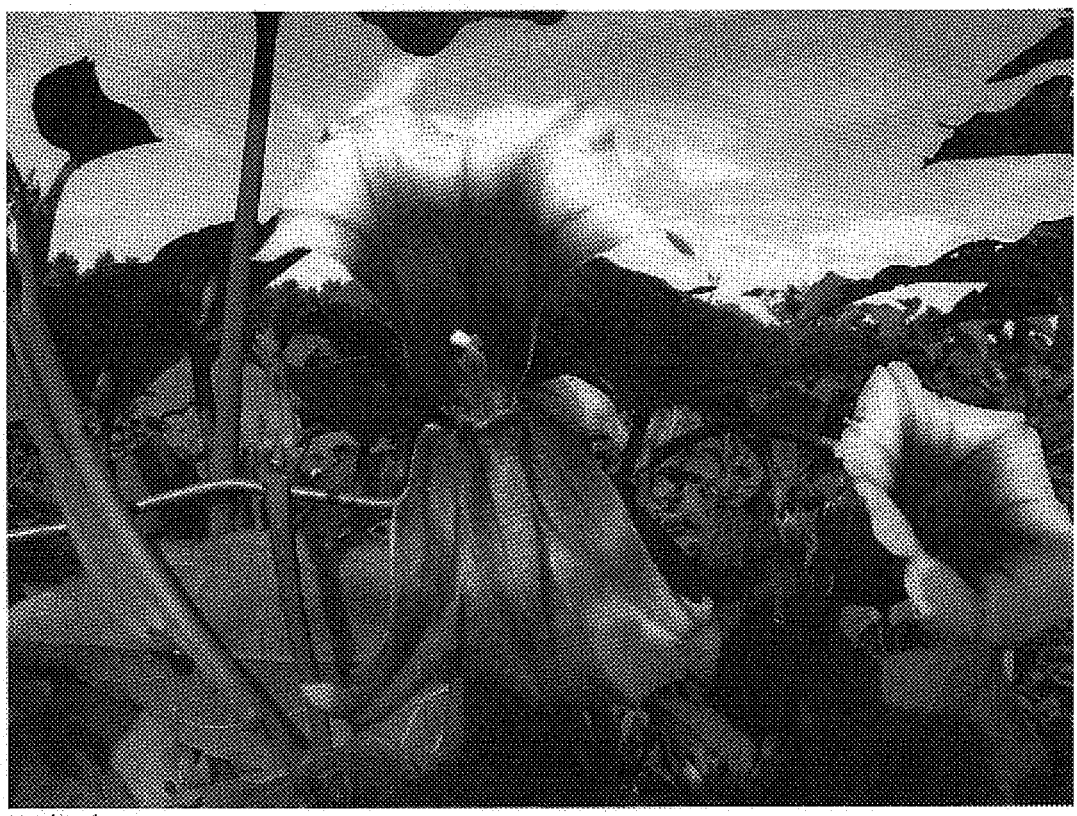
FIG. 6 is a color photograph showing a view of a typical flower of 'Covington' with petals peeled back to reveal internal structures.

Flowers. 'Covington' flowers sporadically throughout the season in response to a variety of stressful conditions (e.g., drought, nutrient stress, cloudy weather). Flowering is enhanced by shorter day lengths, but the precise photoperiod for flower induction is currently unknown. FIGS. 4-6 show views of typical flowers of the variety. The inflorescence is generally a cyme in which there is one solitary peduncle. Peduncles are green (144A to 144B) averaging 40 mm long from mature leaf axils, with an average diameter of 4 mm. Usually buds of the first and second order are developed, but sometimes single flowers are produced. Buds are purple colored (187A) and average 22 mm in length and 7 mm in diameter 24 hours before opening. The corolla is composed of five fused petals that form a funnel with a pentagonal limb. Corolla width is about 4.5 cm and corolla length is about 4.3 cm. The flower has slight to no fragrance. The inner and outer limbs are lavender (76B). The outer throat is lavender (N80B) and the inner throat purple (N80A). There are five sepals with an average length of 9.3 mm and width of 4.5 mm. The sepals are ovate with an acute apex, and both inner and outer sepals are green. The outer sepal color is 144C and the inner sepal color is 144D. Each flower has one pistil with a light purple colored style (76B). The stigma is cream colored (155D) and the style averages about 2 mm wide and 18 mm long. The stigma is slightly exerted relative to the stamens. The ovary is yellow (160B) and superior with two locules that contain one or two ovules. At the base of the ovary there are orange basal glands (167C) containing nectar continuing completely up the ovary. There are five cream colored anthers (155B) that average 2.7 mm long. Pollen is cream (155B) and produced in moderate amounts.

True seed have never been obtained from 'Covington' as the female parent, and it is considered female sterile. A few seed have been produced using it as the male parent, but less than one percent of pollinations have been successful. In practical terms 'Covington' is essentially male sterile. Stained pollen appears normal and the cause of the extremely low fertility is not known.

Figure 7:
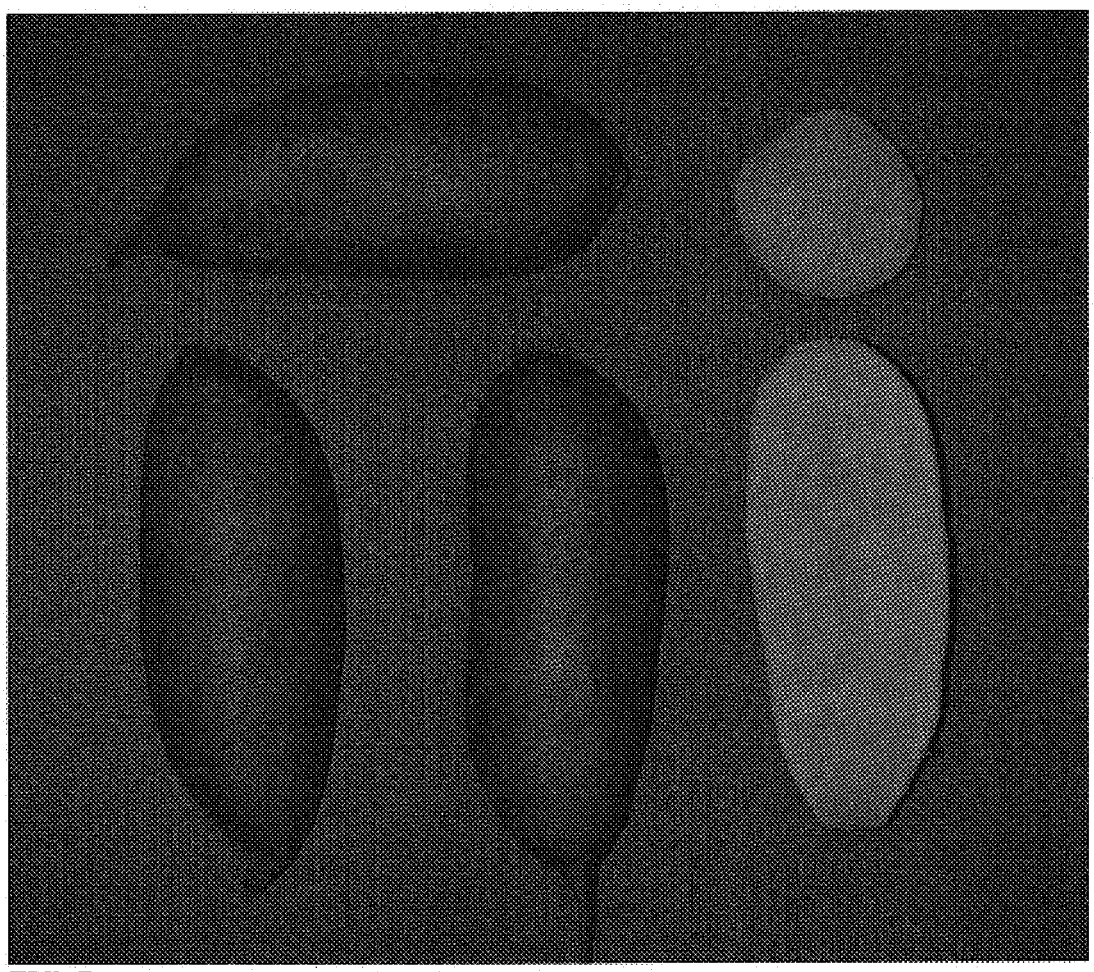
FIG. 7 is a color photograph showing typical storage roots and their flesh color produced by 'Covington'.

Storage Roots. FIG. 7 depicts storage roots of 'Covington'. 'Covington' produces orange-fleshed (28B to 28C), smooth-skinned, storage roots that are generally oblong to elliptic to round elliptic in shape as compared with 'Beauregard'. The skin color of 'Covington' varies from light to medium rose (33D to 34D) and tends to darken on storage. The skin color of 'Covington' is very similar in appearance and color to 'Beauregard' immediately after harvest but its flesh color is typically darker orange.

One of the most desirable attributes of 'Covington' is that it generally produces shorter, more uniformly shaped storage roots compared with 'Beauregard', resulting in higher "pack-out" by sweetpotato packers. The dry matter content of 'Covington' storage roots averages 19-20%, while 'Beauregard' averages 18%-19%.

Culinary Quality. The flavor of the baked storage roots of 'Covington' has been judged to be excellent by standardized and informal taste panels and it typically scores much better in this regard as compared with 'Beauregard'.

Storage Root Yield. Table 2 summarizes the results of 23 yield trials of 'Covington' conducted in North Carolina during 2001-2004. On average, 'Covington' produced 10% greater marketable yield than 'Beauregard' and the pack-out of storage roots scored as U.S. No. 1's was higher. Multiple large-scale (>5 acres) on-farm trials have generally validated these results.

TABLE 2

Average performance of 'Covington' and 'Beauregard' (B94-14) over 23 yield tests conducted in North Carolina during 2001-2004.

| | Total Yield | Marketable Yield | | Size Distribution by Class (Percent of total yield) | | | |
|---|---|---|---|---|---|---|---|
| CLONE | bu/A | Bu/A | % Beau | No. 1 | Canners | Jumbo | Culls |
| 'Covington' (G2-G7) | 751 | 702 | 110 | 60 | 26 | 8 | 7 |
| 'Beauregard' (B94-14 G2) | 797 | 701 | 100 | 54 | 21 | 13 | 12 |

Note:
Percent 'Beauregard' is determined by adding the percentage 'Beauregard' for each test, then dividing by the number of tests. There were two tests where 'Covington' was over 200% of the 'Beauregard' yield; thus the average is higher when calculated by this method than if determined based on the overall average, which would be 100%.

Disease and Pest Resistance. Table 3 summarizes the results of disease evaluations of 'Covington'. Based on multiyear disease evaluations, 'Covington' is resistant to *Fusarium* wilt (*Fusarium oxysporum* Schlect. f. sp. *batatas* (Wollenw.) Snyd. & Hans.), and the russet crack strain of sweetpotato feathery mottle virus, and moderately resistant to *Streptomyces* soil rot (*Streptomyces ipomoeae* (Person & W. J. Martin) Waksman & Henrici) and southern root knot nematode, *Melodogyne incognita* (Kofoid & White), the most important pathogens of sweetpotato in North Carolina.

'Covington' is susceptible to the WDS (wireworm, *Diabrotica, Systena*) complex of insects, which are the major causes of insect damage of sweetpotato in North Carolina.

Voucher Specimens

A tissue culture voucher of 'Covington' will be deposited in the USDA-ARS Sweetpotato Germplasm Repository at the Plant Genetic Resources Conservation Unit, Griffin, Ga., USA, upon patenting.

What is claimed is:

1. A new and distinct cultivar of *Ipomoea batatas* plant named 'Covington' substantially as illustrated and described herein.

* * * * *

UNITED STATES PATENT AND TRADEMARK OFFICE

CERTIFICATE OF CORRECTION

PATENT NO. : PP 18,516 P3
APPLICATION NO. : 11/225431
DATED : February 26, 2008
INVENTOR(S) : Yencho et al.

It is certified that error appears in the above-identified patent and that said Letters Patent is hereby corrected as shown below:

Column 3, In the paragraph titled SUMMARY OF THE INVENTION, Lines 10-14:

Please delete " 'Covington' is also resistant to the russet crack strain of sweetpotato feathery mottle virus and moderately resistant to southern root knot nematode, all of which are considered to be major flaws in the variety "Beauregard'."

And add --'Covington' is also resistant to the russet crack strain of sweetpotato feathery mottle virus, moderately resistant to southern root knot nematode and produces a lower percentage of culls and off-types at harvest, all of which are considered to be major flaws in the variety 'Beauregard'.--

Signed and Sealed this

Ninth Day of December, 2008

JON W. DUDAS
*Director of the United States Patent and Trademark Office*